United States Patent [19]

Vértesy et al.

[11] Patent Number: 5,986,089
[45] Date of Patent: Nov. 16, 1999

[54] PROCESS FOR THE PREPARATION OF MOENOMYCIN A

[75] Inventors: Laszló Vértesy; Andreas Stärk, both of Eppstein; Eberhard Ehlers, Hofheim, all of Germany

[73] Assignee: Hoechst Aktiengesellschaft, Frankfurt am Main, Germany

[21] Appl. No.: 09/061,028

[22] Filed: Apr. 16, 1998

[30] Foreign Application Priority Data

Apr. 17, 1997 [DE] Germany .............. 197 16 013

[51] Int. Cl.[6] ............................. C07H 1/00
[52] U.S. Cl. .............. 536/127; 536/16.8; 536/17.2; 536/17.9; 536/18.5
[58] Field of Search ................. 536/18.5, 127, 536/75, 172, 17.9, 16.3

[56] References Cited

U.S. PATENT DOCUMENTS

| | | | |
|---|---|---|---|
| 3,674,866 | 7/1972 | Lindner et al. | 435/73 |
| 4,684,626 | 8/1987 | Welzel | 519/25 |

FOREIGN PATENT DOCUMENTS

| | | |
|---|---|---|
| 0 355 679 A3 | 2/1990 | European Pat. Off. . |
| 1 236 726 | 3/1967 | Germany . |
| 1 617 466 | 4/1971 | Germany . |
| 37 04 659 A1 | 8/1988 | Germany . |
| 1 068 639 | 5/1967 | United Kingdom . |

OTHER PUBLICATIONS

English language abstract of DE 1 617 466 (Derwent Abstract No. 66–31774F).
English language abstract of DE 37 04 659 A1 (Derwent Abstract No. 88–243156).
English language abstract of EP 0 355 679 A3 (Derwent Abstract No. 90–060448).
English language abstract of DE 1 236 726 (Derwent Abstract No. 66–20187F).
Huber, Gerhard, "Moenomycin and Related Phosphorus–Containing Antibotics," *Antibiotics*, vol. V, Part 1, pp. 135–153 (1979), ed. F. E. Hahn.
Scherkenbeck, Jürgen et al., "Structures of Some Moenomycin Antibotics—Inhibitors of Peptidoglycan Biosynthesis," *Tetrahedron*, vol. 49, No. 15, pp. 3091–3100 (1993).
Wallhausser, K. H. et al., "Moenomycin, a New Antibiotic I. Fermentation and Isolation," *Antimicrobial Agents and Chemotherapy*—1965, pp. 734–737 (Oct. 17–21, 1965).
Welzel, Peter et al., "Moenomycin A: Further Structural Studies and Preparation of Simple Derivatives, " *Tetrahedron*, vol. 39, No. 9, pp. 1583–1591 (1983).

*Primary Examiner*—Elli Peselev
*Attorney, Agent, or Firm*—Finnegan, Henderson, Farabow, Garrett & Dunner, L.L.P.

[57] ABSTRACT

Moenomycin A can be prepared by fermentation of a moenomycin-producing microorganism and subsequent separation of moenomycin A from the other components of the culture filtrate by chromatography, using an anion exchanger as chromatography material.

9 Claims, No Drawings

PROCESS FOR THE PREPARATION OF MOENOMYCIN A

The present invention relates to a process for isolating moenomycin A from microbial culture liquids.

Moenomycin and many of its derivatives have been known for a long time (cf. DE-A 3 704 659, EP 0 355 679, G. Huber in *Antibiotics*, ed. F. Hahn, Springer Verlag, Berlin 1979, Vol. IV, page 135 et seq., Welzel et al. in *Tetrahedron*, 1983, Vol. 39, No. 9. 1583–1591, incorporated by reference herein). Moenomycins, for example moenomycin A, are preferably obtained by fermentation of microorganisms and subsequent purification.

The term "moenomycin" means a complex of moenomycin components (for example as produced by microorganisms) as well as the individual components. Moenomycin A is a component with particular antibiotic activity in the moenomycin complex.

Moenomycin A has the following structural formula:

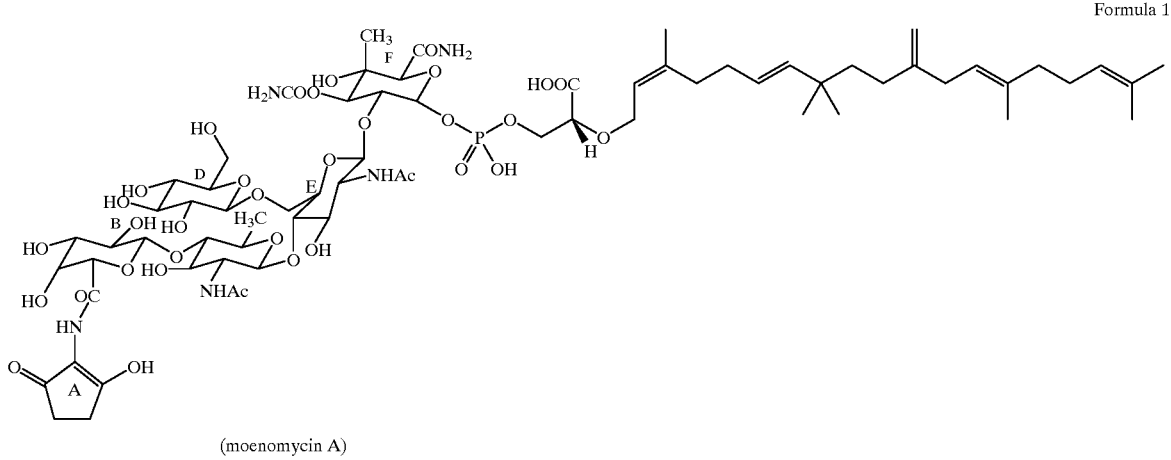

(moenomycin A)

The principal components besides moenomycin A are the components $A_{11}$, $A_{12}$, $C_1$, $C_2$, $C_3$ and $C_4$.

Examples of microorganisms which produce moenomycin complexes are *Streptomyces bambergiensis, S. ghanaensis, S. ederensis* and *S. geysirensis*. *Streptomyces bambergiensis* is particularly preferred (cf. in this connection Huber loc.cit.).

It has recently been found that moenomycin, but especially moenomycin A, is suitable for controlling *Helicobacter pylori* infections (copending application Ser. No. 09/036,683, filed Mar. 9, 1998, incorporated herein in by reference). Infections with *Helicobacter pylori* are the main cause of gastritis and ulcers in humans.

Although the moenomycin complex is suitable for use in human medicine, problems are associated with dosage because of the varying composition of components which is a consequence of the fermentation-dependent microbiological origin. For this reason, there is a need in human medicine for the use of only single compounds (monocomponents) as active substances.

According to "Antimicrobial Agents and Chemotherapy" (1965), 737, it is possible to isolate from the moenomycin complex by chromatography on silica gel columns and elution with propanol/ammonia mixtures after fractionation four components A, $B_1$, $B_2$ and C. These components are also detectable on a thin-layer chromatogram after development of the chromatogram in an n-propanol/2N $NH_3$ (70:30) system and located by spraying with chlorosulfonic acid/glacial acetic acid, showing separate spots with different $R_F$ values. The moenomycin components are very similar to one another chemically and show no differences from the moenomycin complex with respect to solubility, acidic property, color reactions or behavior on paper chromatography and by paper electrophoresis; they differ from one another by their chromatographic behavior on silica gel and by the absence of a characteristic UV absorption with components $B_1$ and $B_2$.

The components ve recently been separated by use of reverse phase (RP) chromatography, for example on LICHROPREP® RP-18 (J. Scherkenbeck et al. *Tetrahedron*, Vol. 49, No. 15 (1993), 3091–3100).

However, none of these laboratory methods is suitable for the industrial isolation of moenomycin components: silica gel chromatography is impractical because it is difficult to reuse the support and because of the price. Likewise, reverse phase chromatography entails very high costs. The use of other separation principles, such as ion exchangers, has hitherto failed owing to the inadequate separation of the moenomycin A component from the C components. The patents GB 1068639 and DE 1236726 describe purification of the moenomycin complex on cellulose-based ion exchangers. However, this purification is not effective in separating the components. In addition, this process can be transferred to the industrial scale only with difficulty, in particular because of the sensitivity of the cellulose support to pressure. German Patent 1 617 466 reports separations of moenomycins D, E, F, G and H on strongly basic polystyrene-based anion exchangers. However, the described process is unsuitable, because of lack of selectivity, for purifying the moenomycin A component. Separation of the A component from the C components is inadequate.

It has now been found, surprisingly, that moenomycin A can be removed from the moenomycin complex at low cost on a large scale by means of anion exchange chromatography.

The present invention accordingly relates to a process for preparing moenomycin A by fermentation of a moenomycin-producing microorganism and subsequent separation of moenomycin A from the other components of the culture filtrate by chromatography, wherein an anion exchanger is used as the chromatographic material.

Preferred anion exchange materials are modified methacrylate copolymers with diethylaminoethyl groups as functional groups.

Particularly suitable anion exchanger materials are the products TOYOPEARL® DEAE-650 S (Tosohaas, Montgomeryville, Pa. 18936) or FRACTOGEL® TSK DEAE-650 S (E. Merck, Darrnstadt, Germany).

The chromatography according to the invention can take place in the pH range from 5 to 9, preferably between pH 7 and 8. Many buffer systems effective in said pH range are suitable for the separation, such as phosphate, citrate, Tris/HCl buffer or others.

The moenomycin components can be eluted (desorbed) from the anion exchanger using increasing salt gradients, preferably 0 to 4, in particular 0 to 2, molar gradients. Particularly suitable salts are NaCl and KCl.

It may furthermore be worthwhile to use decreasing pH gradients, preferably from pH 9 to pH 3, in particular from pH 8 to pH 4.5. A pH gradient of this type can be produced by, for example, starting from $\frac{1}{15}$ M $Na_2HPO_4$ (pH~8) and changing linearly to $\frac{1}{15}$ M $KH_2PO_4$ (pH~4.9) as buffer in a manner known per se.

Anion exchange separation can also, where appropriate, be carried out with buffer systems which contain a proportion of an organic solvent. Examples which can be used are aliphatic alcohols such as, for example, methanol, ethanol, the propanols or others, in concentrations of from 0 to 95%, preferably from 15 to 40%. The capacity of the ion exchanger decreases with increasing organic solvent concentration, and thus elution of the moenomycin components is also possible with a gradient in which the percentage of solvent increases. Of the moenomycin components, moenomycin A is least strongly bound by the support according to the invention, with the result that this compound is isolated first on elution.

Initial purification of the culture filtrate is advantageous prior to the separation of moenomycin A according to the invention by means of anion exchangers. This previous purification can take place by use of a neutral adsorption resin. Examples of suitable neutral adsorption resins are MCI GEL® CHP20P and DIAIONE® HP 20SS (Mitsubishi Chemical Corporation) or AMBERLITE® XAD 16 and XAD 1180S (Rohm & Haas). This entails bringing the culture filtrate into contact with the adsorption resin, separating the loaded resin from the extracted culture filtrate, and eluting (desorbing) the antibiotics using mixtures of organic solvents in water in a manner known per se. An initial purification of this type on a neutral adsorption resin removes salts and lipids from and concentrates the crude moenomycin and is thus beneficial for the separation efficiency of the ion exchanger step.

Another method for initial purification consists of extracting the culture filtrate, where appropriate in concentrated or dried form, with a nonpolar solvent, in which case nonpolar impurities dissolve in the nonpolar solvent. Examples of suitable nonpolar solvents are petroleum ether, acetone, methyl ethyl ketone and others. The moenomycin complex can then be extracted from the remaining culture filtrate using a polar solvent such as, for example, methanol. The concentration or drying of the culture filtrate which is worthwhile where appropriate takes place, for example, by distillation, ultrafiltration, spray drying or freeze drying.

In order to increase the efficiency the extraction with polar solvent, it may be worthwhile to add a complexing agent such as EDTA, citric acid or the like to the culture filtrate. The complexing agent reduces the concentration of multiply-charged ions which, with moenomycin, form salts which are of low solubility in the polar solvent.

Advantageous procedures for concentrating the moenomycin or moenomycin A are described in Examples 1 and 2.

The previous purification and subsequent separation of th components on a modified methacrylate copolymer DEAE support results in salt-containing moenomycin A solutions which may be contaminated with small amounts of other components, in particular moenomycin $A_{12}$. The purity of the moenomycin A is from 90 to more than 99%, depending on the composition of the eluate from the component-separating column. It is advantageous to again use for the final purification (i.e. reduction in concentration of the remaining additional components and removal of salts) neutral adsorption resins such as, preferably, MCI GEL® CHP20P, or DIAION® HP20SS or AMBERLITE®XAD 16 or XAD 1180 S. Fractionations on such resins using aqueous buffer/organic solvent mixtures such as, for example, phosphate buffer/isopropanol mixtures can result in considerable purifications of the moenomycin A. Thus, for example, only incompletely concentrated moenomycin A can be refined to a purity of more than 99%. Many buffer substances which buffer adequately between pH 4 and 10, preferably between pH 7 and 9, are suitable.

Suitable organic solvents are water-miscible solvents such as lower alcohols, acetone, acetonitrile and the like.

The removal of salts from the salt-containing moenomycin A solutions can take place by use of said neutral adsorption resins. After loading at pH values between 7 and 9, the elution is carried out with water to which increasing proportions of a water-miscible organic solvent have been added. The moenomycin A-containing column eluate with sufficiently pure component is collected, concentrated by ultrafiltration or distillation, preferably in vacuo, and dried. Moenomycin A obtained in this way has a purity of more than 97%. The main impurity remaining is moenomycin component $A_{12}$.

In order to obtain a higher percentage content of moenomycin A, it is possible to repeat the purification steps of ion exchange chromatography and component purification on adsorption resins. The resulting moenomycin is ≧99% pure.

Depending on the salts and buffer chosen for the separations, the antibiotic may be in the form of a sodium, potassium, or an ammonium salt, or of another salt. The preferred counter ion (cation) can be chosen freely, depending on the pharmaceutical requirements.

The following Examples explain the present invention in detail.

EXAMPLE 1

Concentration of Moenomycin From the Culture Filtrate by Solid Phase Extraction

Fermentation of a mutant of *S. ghanaensis* (ATCC 14672) carried out by a method based on that of K. H. Wallhaiuser et al., *Antimicrobial Agents and Chemotherapy* (1965), pages 734–736, and filtration by means of a Simex filter press, washing with deionized water and clarification by filtration through KS 80 multilayer filters result in 1,100 L of moenomycin-containing culture filtrate. Solid contents represent ~20g/L with 2.8 g of moenomycin A. Conductivity: 14 mS/cm, pH 7.5.

150 L with 3 kg of solids and 420 g of moenomycin A are loaded onto a column with a capacity of 58 L (W×H=33.3 cm×66 cm) and packed with MCI GEL® CHP20P adsorption resin. Flow rate: 2.5 L per minute. The adsorption is followed by elution with a gradient containing 0 to 40% isopropanol in water at a flow rate of 10 L per minute. The fractions containing predominantly moenomycin A are combined, concentrated by ultrafiltration and dried, resulting in 0.7 kg of the moenomycin complex.

EXAMPLE 2
Concentration of Moenomycin From the Culture Filtrate by Selective Dissolution.

1,000 liters of culture filtrate prepared as in Example 1 are concentrated to 140 L by ultrafiltration using a "UF-36-9 industrial pilot plant" (DDS). The membranes used are 9 m$^2$ NADIR® PA 20 H layers. The ultrafiltration rate (flow rate) is 28 liters per m$^2$ per hour. When the retentate volume reaches 140 L, the concentrate is continuously washed with a total of 140 L of deionized water. The conductivity of the concentrate falls to 1.8 mS/cm during this. The final concentration of the moenomycin complex in the retentate (140 L) is 32.9 g per liter, and the pH is 6.9. The retentate is spray dried. The ultrafiltrate (permeate) contains 24 mg of moenomycin per liter, in total 24 g, corresponding to 0.52% of the actual amount. The final product (the dried retentate) is a pale brown powder, weighs 15 kg and contains 2.8 kg of moenomycin A (99% of the A component employed).

3 kg of the spray-dried product are stirred with 50 L of acetone and centrifuged. The organic extract contains 1.02 kg of lipids. The undissolved residue is stirred 3 times with 20 L of methanol for 1 hour each time and then filtered off. Moenomycin A (0.54 kg) is present in the methanol phases. Conductivity of a 1% strength solution of the substance freed of methanol (1.1 kg):1 mS/cm. The methanolic extract can, after concentration in vacuo and dilution with water, be employed directly for separating the components.

EXAMPLE 3
Separation of Moenomycin Components A and C by Ion Exchange Chromatography 1 kg of moenomycin complex is dissolved in 20 L of water (pH 7.4) and loaded onto a column packed with 20 L of FRACTOGEL® TSK DEAE-650 anion exchanger equilibrated at pH 7.4. It is first washed with buffer A (20 mM phosphate buffer, pH 7.4. 2.5 mS+20% 2-propanol) and then a linear gradient from buffer A to buffer B (=1 M NaCl in buffer A) is applied. The flow rate in this test is 7 L/minute, equivalent to 21 column volumes per hour, and the fraction size is 20 L (~1 column volume). After removal of salts from the fractions containing predominantly moenomycin A by ultrafiltration and drying, the separation affords 480 g of component A with a purity of 95%. The recovery rate for the moenomycin components is greater than 90%.

EXAMPLE 4
Removal of Salts on Adsorption Resins for Moenomycin A Separated on the Anion Exchanger 81 g of 95% pure moenomycin A dissolved in 7 L of aqueous buffer solution, pH 7.9, 10.5 mS/cm, as results after DEAE purification and ultrafiltration, are loaded onto a column with a capacity of 2.7 L (W×H=10 cm×35 cm) and packed with MCI GEL® CHP20P. Elution is carried out with a gradient containing 0–35% isopropanol in water. The fractions containing 97% moenomycin A are combined, concentrated by ultrafiltration and freeze dried. 55 g of 98.5% pure moenomycin A are obtained in addition to 24 g of 88% pure material.

EXAMPLE 5
Further Purification of the Moenomycin A on an MCI GEL® CHP20P Adsorption Resin 81 g of 95% pure moenomycin A dissolved in 7 L of aqueous buffer solution, pH 7.9, conductivity 10.5 mS/cm (resulting from DEAE purification and ultrafiltration), are loaded onto a column with a capacity of 2.7 L (W×H=10 cm×35 cm) and packed with MCI GEL® CHP20P. Elution is carried out with a linear gradient from buffer A (m/15 phosphate buffer, pH 7.8) to buffer B (m/15 phosphate buffer, pH 7.8 with 33% 2-propanol). The column flow is fractionated and analyzed. The fractions with at least 98.8% pure moenomycin A are collected and, after removal of the salts as described in Example 4, dried, resulting in 71 g of 99.3% pure moenomycin A with 0.4% moenomycin $A_{12}$ as concomitant substance.

We claim:

1. A process for preparing moenomycin A, comprising fermenting a moenomycin-producing microorganism in culture, obtaining culture filtrate, and subsequently separating moenomycin A from the other components of the culture filtrate by chromatography, wherein anion exchange material is used as chromatographic material.

2. The process of claim 1, wherein the anion exchange material is a modified methacrylate copolymer.

3. The process of claim 2, wherein the modified methacrylate copolymer has diethylaminoethyl groups as functional groups.

4. The process of claim 1, wherein a salt solution with an increasing salt content from 0 to 4 molar is used as eluent.

5. The process of claim 1, wherein a solvent with a pH decreasing from pH 9 to pH 3 is used as eluent.

6. The process of claim 1, wherein the culture filtrate is, before the anion exchange chromatography, subjected to an initial purification by chromatography on a neutral adsorption resin.

7. The process of claim 1, wherein the culture filtrate is, before the anion exchange chromatography, subjected to an initial purification by extraction with a nonpolar solvent.

8. The process of claim 1, wherein the resulting moenomycin A is further purified by at least one other chromatography step on a neutral adsorption resin.

9. A process for preparing moenomycin A, comprising fermenting a moenomycin-producing microorganism in culture, obtaining the culture filtrate, purifying the filtrate by chromatography on a neutral adsorption resin, and subsequently separating moenomycin A from the other components of the culture filtrate by chromatography, wherein an anion exchange material is used as the chromatographic material.

* * * * *